US006913921B2

(12) United States Patent
Fischer

(10) Patent No.: US 6,913,921 B2
(45) Date of Patent: Jul. 5, 2005

(54) RAPID CELL BLOCK EMBEDDING METHOD AND APPARATUS

(75) Inventor: Andrew H. Fischer, Stow, MA (US)

(73) Assignee: University of Massachusetts, Worcester, MA (US)

( * ) Notice: Subject to any disclaimer, the term of this patent is extended or adjusted under 35 U.S.C. 154(b) by 0 days.

(21) Appl. No.: 10/697,993

(22) Filed: Oct. 30, 2003

(65) Prior Publication Data

US 2004/0121456 A1 Jun. 24, 2004

Related U.S. Application Data

(60) Provisional application No. 60/422,768, filed on Oct. 31, 2002.

(51) Int. Cl.[7] .............................................. C12M 1/12
(52) U.S. Cl. .............................. 435/308.1; 435/297.2; 435/307.1; 422/101
(58) Field of Search ............................ 435/40.5, 40.52, 435/284.1, 286.5, 287.9, 288.1, 288.3, 297.2, 297.5, 304.1, 305.1, 307.1, 308.1, 305.4; 422/99, 101, 102; 118/50, 429; 210/406, 416.1, 419, 428

(56) References Cited

U.S. PATENT DOCUMENTS

| 2,923,669 | A | | 2/1960 | Poitra |
| 3,227,130 | A | * | 1/1966 | Weiskopf ............... 118/697 |
| 4,557,903 | A | | 12/1985 | McCormick |

(Continued)

FOREIGN PATENT DOCUMENTS

DE 2928790 A * 2/1981 ............ G01N/1/28
JP 2000146782 A * 5/2000 ............ G01N/1/28

OTHER PUBLICATIONS

Diaz–Rosario, Luis A. et al, "Cell Block Preparation by Inverted Filter Sedimentation is Useful in the Differential Diagnosis of Atypical Glandular Cells of Undetermined Significance in ThinPrep Specimens," *Cancer*, 90(5): 265–272 (2000).
Fahey, Colleen et al, "Collodion Bag: A Cell Enhanced Cell Collection," *Laboratory Medicine*, 74(2): 94–96 (1993).
Srinivasan, Mythily et al, "Effect of Fixatives and Tissue Processing on the Content and Integrity of Nucleic Acids," *American Journal of Pathology*, 161(6): 1961–1971 (2002).
Yang, Grace C.H. et al., "Use for Body Fluids, Fine Needle Aspirations and Endometrial Brush Biopsies," *Acta Cytologica*, 42(3): 703–706 (1998).

*Primary Examiner*—William H. Beisner
(74) *Attorney, Agent, or Firm*—Nutter, McClennen & Fish LLP

(57) ABSTRACT

A method and apparatus for embedding cells that utilizes a flow-through embedding technique maximizes the efficiency of extractions and decreases time for embedding the cell fragments, minimizes cell loss, and automatically positions cell samples at the position in which a microtome blade will section them. The apparatus includes a cell flow pathway defined by an inflow tube for delivering cell fragments from a cell sample to a sample port. The sample port is in fluid communication with a tissue cassette having attached thereto a filter. The cell flow pathway is in communication with a reagent flow pathway for delivering the reagents through the sample port to the cassette. The apparatus is configured such that the application of pressure directs the cell fragments from the cell sample through the cell flow pathway, and effects delivery of the reagents through the reagent flow pathway. The apparatus produces an embedded cell block having concentrated cells near the plane of the block to be sectioned in a quick and efficient manner.

18 Claims, 4 Drawing Sheets

U.S. PATENT DOCUMENTS

| | | |
|---|---|---|
| 4,569,647 A | 2/1986 | McCormick |
| 4,604,964 A | 8/1986 | Gordon et al. |
| 4,656,047 A | 4/1987 | Kok et al. |
| 5,080,869 A | 1/1992 | McCormick |
| 5,137,710 A | 8/1992 | Smalley et al. |
| 5,269,671 A | 12/1993 | McCormick |
| 5,354,370 A | 10/1994 | Schmehl |
| 5,665,398 A | 9/1997 | McCormick |
| 5,691,633 A * | 11/1997 | Liu et al. .................. 324/71.1 |
| 5,817,032 A | 10/1998 | Williamson, IV et al. |
| 5,928,934 A | 7/1999 | McCormick |
| 6,207,408 B1 | 3/2001 | Essenfeld et al. |
| 6,395,234 B1 | 5/2002 | Hunnell et al. |
| 6,413,767 B1 | 7/2002 | Izvoztchikov et al. |

* cited by examiner

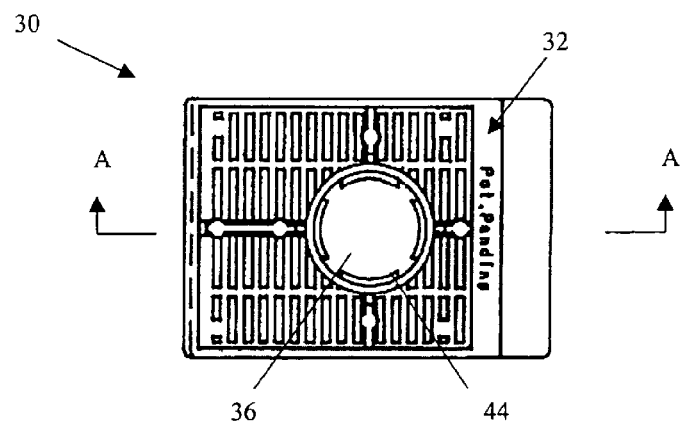
FIG. 3A
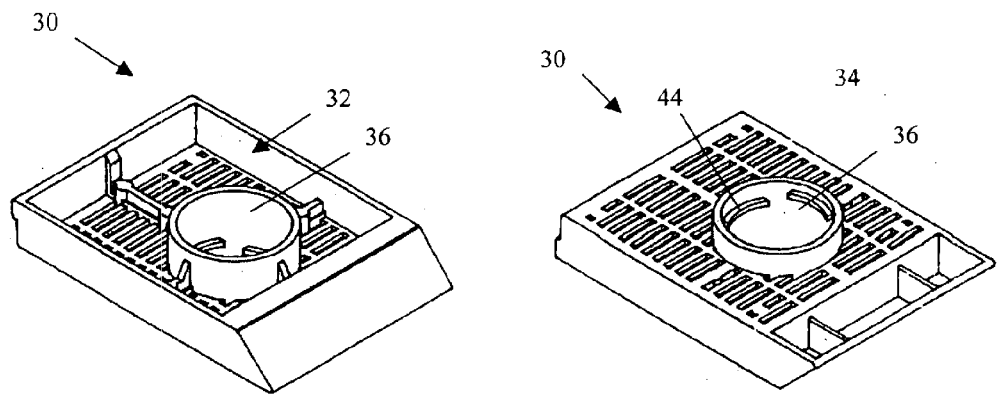
FIG. 3B  FIG. 3C

RAPID CELL BLOCK EMBEDDING METHOD AND APPARATUS

CROSS-REFERENCE TO RELATED APPLICATIONS

This application is based on U.S. provisional application No. 60/422,768 entitled "Automated Cell Block Embedding Apparatus" and filed on Oct. 31, 2002, of which priority is claimed.

FIELD OF THE INVENTION

The present invention relates to methods and devices for preparing cells for microscopic examination, and for archiving the cells for molecular and immunologic tests. More particularly, the invention relates to a method and apparatus for embedding cells and tissue fragments within a solid substrate, such as paraffin, to enable them to be cut with a microtome for microscopic evaluation, and to be stored in a stable state.

BACKGROUND

Many disease processes can only be diagnosed on the basis of histologic or cytologic examination using a light microscope. For instance, while the presence of a tumor can be detected using radiological devices, the determination of whether a tumor is benign or malignant still requires a pathologist's interpretation of the appearance of the cells using light microscopy. Before reaching this stage, however, the tissue sample must first be retrieved, collected, and processed for microscopic examination. A number of techniques are available for retrieving and collecting biopsies or cell samples from a patient. It is of benefit to patients to use minimally invasive techniques for obtaining biopsies or cell samples. For example, small tissue fragments can be obtained from fine needle aspiration biopsy, or by brushing body cavity surfaces accessible through minimally invasive endoscopic techniques. Once retrieved, the cells then need to be processed for microscopy. A variety of processing techniques are known, including the cytospin® technique and the thin-prep® technique for depositing tissue fragments directly onto a microscope slide.

Another technique, commonly referred to as a cell block preparation, has several advantages over the direct deposition of tissue fragments. The cell block procedure immobilizes cells or small tissue fragments in a solid support, typically paraffin wax. Thin sections of the cell block are then cut with a microtome and the sections mounted onto a microscope slide for examination. The resulting sections from the cell block display diagnostic information in a manner that complements the direct deposition techniques. For example, the architectural arrangements of cells to each other is displayed better in section from a cell block than in directly deposited cells on a microscope slide. Cell blocks also permit important diagnostic molecular and immunological tests to be conducted on the cell samples that would otherwise be difficult or impractical on direct preparations. In addition, cell blocks appear to preserve the cells indefinitely in a convenient manner at room temperature, thereby facilitating biomedical research.

The cell block preparation method requires that the cell fragments be "embedded" in a solid medium, most commonly paraffin wax. "Embedding" requires the following generic steps: (1) all water molecules must be removed from the cells, typically by alcohol (water is miscible with alcohol); (2) all alcohol must then be removed, as well as all fatty substances, and replaced typically by xylene (xylene is miscible with alcohol but not water); (3) the xylene must be removed and replaced with wax (wax is miscible with xylene but not with most alcohols or water); and (4) the cells in molten wax must then be manually organized and hardened on the underside of a tissue cassette so that a section of the wax block with the embedded tissue can be cut using a microtome. The first three of these steps are commonly performed by a "tissue processor," a machine that circulates alcohol, xylene, and molten wax sequentially in a chamber containing the tissue cassette. Tissue cassettes typically serve the dual purpose of containing the cell sample during the embedding process, and for providing an attachment mechanism for holding the wax block on the microtome machine so that the cell sample subsequently embedded in wax on the undersurface of the cassette is able to be cut into thin sections.

Before "embedding" can take place, the cell sample must be manipulated to concentrate the cells and facilitate their transfer through the embedding procedure. A commonly used procedure for preparing such cell blocks is the clot technique, which is described by Yang et al. in *Acta Cytologica*, 42:703–706 (1998). The clot technique involves the following generic steps: (1) a cell sample is centrifuged for 10 minutes; (2) the supernatant is manually poured off, leaving a concentrated cell button; (3) fibrin and thrombin, obtained from blood bank supplies, is manually added to the cell button and incubated for 15 minutes with occasional manual swirling to trap the cell button into the clotting fibrin; (4) the clotted cell sample is removed manually from the centrifuged tube with care to avoid cell loss due to streaking the clot along the side of the tube or breaking the clot into impractically small pieces; (5) the clotted cell sample is manually transferred to lens paper, which is then folded over and placed manually into a tissue cassette; (6) the tissue cassette is then manually placed into an automated tissue processor, which then cycles alcohol, xylene and hot paraffin into the machine (as described in the preceding paragraph) and is typically set to operate overnight; (7) the following morning, the cassette is manually removed from the liquid paraffin of the tissue processor and opened; (8) the lens paper is opened, and the cell clot is scraped off the lens paper and manually placed into a tissue section mold; and (9) paraffin is gently added to the mold while manually trying to maintain the cell clot against the lowest surface of the mold that will eventually be cut. (10) The tissue cassette is then inverted over the mold to serve as a holder for the microtome machine, and hardened into the wax along with the cell clot. (11) The tissue cassette, with included wax-embedded cell fragments, is then separated from the mold. At this point, the wax block is ready to be cut with a microtome. Many of these eleven steps are common to other existing cell block production techniques.

Another popular procedure for preparing cell blocks is the collodion bag technique, which is described by Fahey and Bedrossian in *Laboratory Medicine*, 74(2):94–96 (1993). The collodion bag technique involves all of the eleven steps above with the exception that steps 1–4 are replaced by the following: Collodion is manually poured into a centrifuge tube to coat the tube. The cell sample obtained from the patient is then centrifuged in the coated tube. The supernatant is poured off, and the thin coating of collodion is pulled from the tube with the included concentrated cell button and embedded as in steps 5–11 above. The collodion technique provides an advantage over the clot technique by avoiding dilution of the cells with fibrin and thrombin. With the collodion technique, no waiting is required for the cell clot to form as is required of the clot technique, and cells are not susceptible to being lost as they are pulled out of the centrifuge tube. However, the collodion technique is substantially more dangerous than the clot technique due to the flammable nature of collodion and its ether solvent.

Yet another technique for preparing cell blocks is described by Diaz-Rosario and Kabawat in *Cancer*, 90:265–272 (2000). In this technique, the cell sample is initially filtered and the filtered sample is scraped from the filter and transferred onto lens paper which is then folded and placed into a tissue cassette and transferred to a tissue processor, followed by steps 6–11 above.

Currently available cell block preparation techniques such as the ones previously described suffer from a number of problems that make them cumbersome, costly, susceptible to contamination or mislabeling, and inefficient for showing diagnostic cells in the final microtome sections. For instance, many of the techniques require that the wax-embedded cell fragments be manually transferred to a tissue cassette required to hold the wax block onto the microtome for sectioning. This manual transfer to the tissue cassette takes a considerable amount of time, as does the step of transferring the cells from a sample tube into a tissue processor. Many of the cell fragments are wasted during the transfer and/or embedding steps. In the past, techniques attempting to improve the concentration of cells within the sectionable material and avoid cell waste have proven less than ideal, because the techniques necessarily involve dilution of the microtome section with carrier substances such that relatively few cells are present, or do not decrease cell loss in pre-embedding steps.

Current cell block techniques typically take anywhere from 8 to 16 hours to complete because the extraction of water, alcohol, fats, and xylene in the tissue processor is time consuming. While there are methods to speed up the tissue processing step (step 6 above), such as by using microwave radiation, vacuum pressure, elevated temperatures, and more rapidly diffusing chemicals, these methods suffer from their own set of problems. These techniques only modestly decrease the tissue processing time (step 6 above) but are relatively tedious to establish in the laboratory. Furthermore, these techniques do not enhance the efficiency of the other processing steps. The ability to produce same-day cell blocks would enable faster diagnoses to be rendered, with cost savings amplified throughout the health care system.

Another drawback with the cell block techniques described above are that they are also susceptible to mislabeling of a sample since the sample has to be manually moved between the sample tube, lens paper (or collodion, and other carrier substances), tissue cassette, and tissue mold. In addition to a susceptibility to complete mislabeling, cross contamination between the patient's sample and cells and biomolecules (including cancer cells) of other sources is also possible with existing techniques. That is, in the fibrin clot technique, the patient's cells are mixed with pooled plasma from other patients in order to form a clot. During transfer of cells to and from the tissue cassette, contamination of cells from one case to another can occur on the forceps used to manually handle the cell buttons. Since multiple tissue cassettes are simultaneously immersed in a common bath of reagents in tissue processors, the possibility for cross contamination of cancer cells from one patient to the cell button of another sample (referred to by pathologists as "floaters") is a well-recognized serious problem.

Yet another disadvantage of current tissue processor steps is that these steps are difficult to standardize. This is because one tissue processing machine typically circulates the embedding reagents for many laboratory samples at one time. A cell block ready to be placed on a tissue processor at 9 AM would necessarily be exposed to different conditions from a sample placed on the same processor at 9:30 AM. Emerging molecular techniques require standardized processing for optimal performance.

Since light microscopy is currently the "gold standard" for diagnosis of many diseases, advances in understanding of the molecular biology of diseases and their treatments generally requires the ability to simultaneously study the microscopic features of cells while preserving their constituent molecules for research. Simultaneous preservation of morphology and the biochemical constituents of a cell currently pose a number of problems for researchers and diagnostic pathologists (reviewed in Srinivasan M, Sedmak D, and Jewell S. "Effect of fixatives and tissue processing on the content and integrity of nucleic acids ". *Am J Pathol.* 2002; 161:1961–71.) Freezing tissues preserves nucleic acids and proteins (though some autolysis is inevitable during the thawing of the tissue), but frozen tissue presents obstacles to morphologic assessment. Some of the obstacles include "freezing artifacts" that distort morphology and hinder classical light microscopy diagnosis, technical difficulties in cutting thin sections of frozen tissue, inability to cut a histologic section from certain types of frozen tissues (for example tissues containing abundant fats), cumbersome and expensive storage of frozen tissue samples, impracticality of freezing very small tissue samples, and the expense of special microtomes needed to cut frozen tissues. Paraffin-embedded cell samples provide excellent morphology and biomolecules such as nucleic acids and proteins appear very stable for long term storage even at room temperature, if the biomolecules survive the embedding steps. Unfortunately, formaldehyde fixation, widely used as a fixative in production of a paraffin embedded tissue block, causes extensive damage to nucleic acids and proteins. While there are paraffin embedding techniques that do not use formaldehyde, these techniques still pose problems. The problems include the slow rate of diffusion of the embedding reagents which permits degradation of biomolecules, day to day variation in fixation conditions when a bulk embedding reagent is used over many days to embed samples, and the potential for contamination of cells from one sample into another as samples are bathed together in vats of the reagents in existing paraffin embedding techniques.

There is thus a need for a cell block preparation technique that is able to place cell fragments within a concentrated area within the cell block, without losing cells, such that a single section of the wax cell block shows a substantial proportion of all the cell fragments without dilution by fibrin or other carrier molecules. Also desirable is a technique which avoids or eliminates mislabeling of a cell block, contamination of one cell block with another cell block, and which requires less embedding reagents and time than currently available techniques, and allows standardized preservation of biomolecules for diagnostic studies and research.

SUMMARY OF THE INVENTION

The present invention provides a method and apparatus that utilizes a flow-through processing and embedding technique for rapidly embedding cells. This flow-through processing maximizes the efficiency of cell recovery and of extractions during embedding, thereby decreasing the amount of cellular sample required, minimizing the amount of time for processing, and minimizing the amount of reagents needed for embedding. The method and apparatus also automatically places cells at the plane in the cell block where they need to be sectioned without diluting them with carrier substances. In addition, the method and apparatus minimizes or eliminates the potential for mislabeling of a cell block or cross contamination between two different cell samples. Finally, the method allows customization and standardization of cell preservation or cell embedding conditions to facilitate cell research.

According to an exemplary embodiment of the present invention, the apparatus includes a modified tissue cassette that serves a dual function of capturing the cell sample and also providing a pathway through which the embedding reagents can flow. A cell flow pathway is provided for delivering cell fragments from a collected cell sample, typically in either an aqueous solution or a liquid cell-preservative, through the modified tissue cassette to a filter that traps the cells and tissue fragments. The apparatus also includes a reagent flow pathway configured to sequentially pass embedding reagents, then lastly paraffin, through the tissue cassette and through the cell sample deposited on the filter. When the paraffin is cooled, the filter is peeled away from the paraffin embedded cells, and a gasket between the filter and the tissue cassette is pulled away from the tissue cassette. This technique leaves a disk of wax protruding from the tissue cassette with the embedded cells placed at the plane at which a tissue section can be cut using a standard microtome. By placing the filter at the plane of the tissue section, the process of manual embedding is eliminated, and the time required for a technician to find the plane of the cells in the embedded block is reduced. Since no other supporting matrix material is used, the cell fragments are not "diluted" with matrix, and each tissue section can therefore show a higher concentration of cells.

The apparatus can be operated manually or be fully automated. A method is also provided for operating and automating the apparatus of the present invention

BRIEF DESCRIPTION OF THE DRAWINGS

The invention can be more fully understood from the following detailed description taken in conjunction with the accompanying drawings, in which:

FIG. 3A is a perspective view of a tissue cassette of the present invention;

FIG. 3B is a top-down view of the tissue cassette of FIG. 3A;

FIG. 3C is a bottom-up view of the tissue cassette of FIG. 3A; and

DETAILED DESCRIPTION OF THE INVENTION

Figure 1:
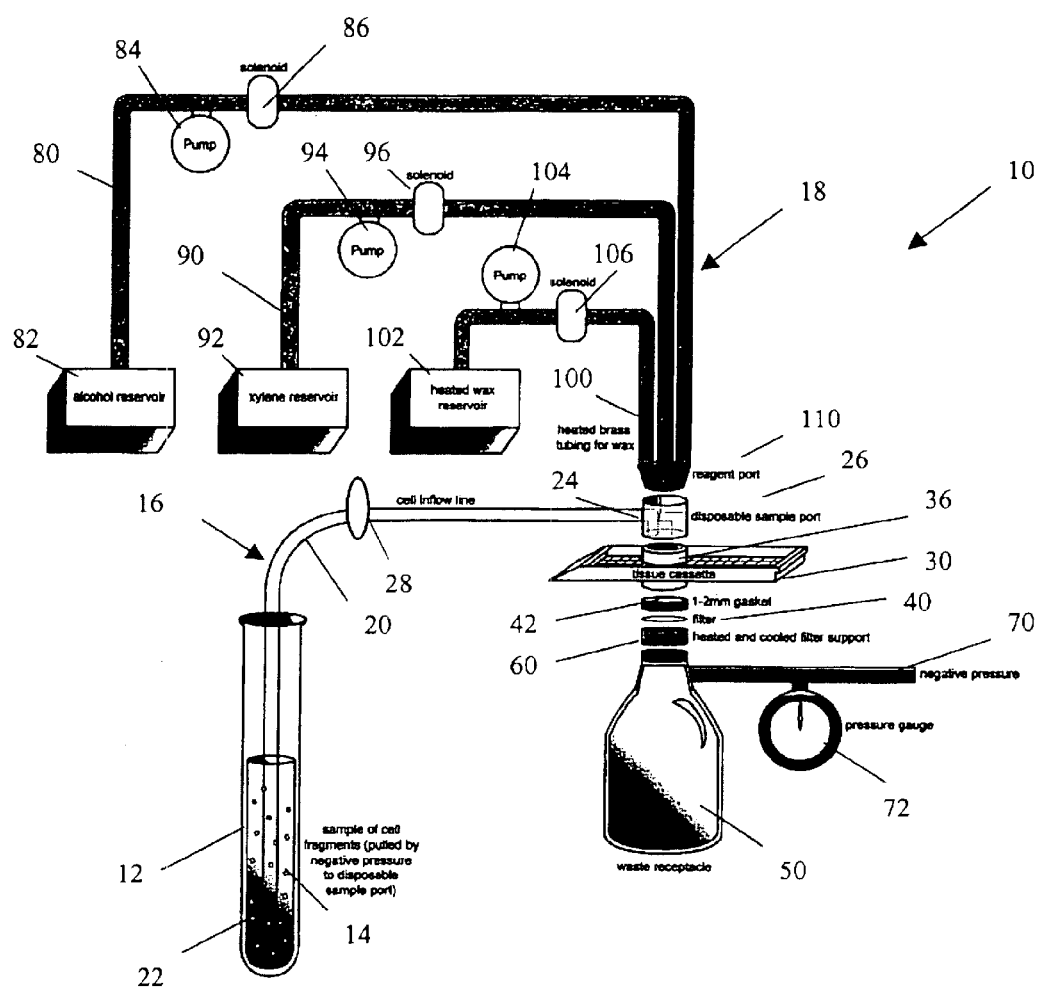
FIG. 1 is a detailed view of a cell block embedding apparatus of the present invention.

The present invention provides a method and apparatus for rapidly preparing a cell block for sectioning with a microtome. The cell block embedding apparatus 10 of the present invention is designed as a flow-through system. As shown in detail in FIG. 1, the apparatus 10 comprises a cell flow pathway 16 defined by an inflow tube 20 which has an inlet end 22 configured for placement within a container 12 holding a cell sample 14 therein and an outlet end 24 which removably connects to a disposable sample port 26. A solenoid tube clamp 28 can be disposed along the inflow tube 20 for regulating the flow of fluid through the tube 20. The container 12 can comprise any suitable shape, form, or size. For example, and as illustrated, the container 12 can be a standard 50 ml disposable centrifuge tube. The cell sample 14 can be in suspension in a physiologic saline solution such as Hanks buffered saline, or in a liquid preservative such as 50% aqueous alcohol. The cell suspension can be vortexed immediately before initiating processing to have the cells suspended. In addition, the cell sample 14 can also be mechanically shaken during the subsequent steps to maintain them in a suspension, for example, by attaching the cell sample container 12 to a mechanical shaker (not shown), or by having a disposable mechanical stirring rod immersed in the cell sample container 12 (not shown).

In fluid communication with the sample port 26 is a disposable reagent port 110 which forms the terminal end of a reagent flow pathway 18 of the apparatus 10. The reagent flow pathway 18 is defined by a plurality of reagent delivery tubes or lines extending from the source of their respective reagents and which then converge at the reagent port 110. Embedding reagents 82, 92 and 102 flow to the reagent port 110 through flow lines 80, 90 and 100, respectively, which are in fluid communication with the reagent port 110. Each of the flow lines 80, 90, 100 can also include a pump 84, 94, 104 for controlling the delivery of the reagent, and a solenoid tube clamp 86, 96, 106 for ensuring an air-tight pathway. In one embodiment, alcohol contained in a reservoir 82 can pass through the alcohol flow line 80 xylene contained in a reservoir 92 can pass through a xylene flow line 90, and melted paraffin can pass from a heated wax reservoir 102 through a heated wax flow line 100 to the reagent port 110. The heated wax flow tube 100 can be formed from brass or other heat-conducting materials, while the alcohol and xylene delivery tubes 80, 90 can be formed from a suitable material which is not degraded by the reagents, such as nylon.

While three different reagent flow lines are shown and described, it is understood that the reagent flow pathway 18 can comprise any number or combination of reagent delivery tubes. In addition, a number of other reagents can also be used in the present invention. For instance, tubes for delivering formalin or decalcifying acid solutions can also be included. Tubes for the delivery of immunohistochemistry reagents can also be applied with the apparatus 10 of the present invention, thereby enabling protein detection. These tubes can be connected to the reagent port 110 in the same manner as for the alcohol and xylene. Furthermore, it is also possible to have a plurality of reagent delivery tubes for delivering the same reagent, if so desired.

The sample port 26, cell inflow tube 20 and its removable outlet end 24, and the cell sample container 12 of the present invention are all disposable, and used for processing only one sample. A baffle can be placed in the disposable sample port 26 to separate the outlet end 24 of the inflow tube 20 from the reagent port 110. This baffle would prevent the cell sample from contaminating the reagent port 110, allowing the reagent port 110 to be used for the subsequent processing of many cell samples.

Figure 4:
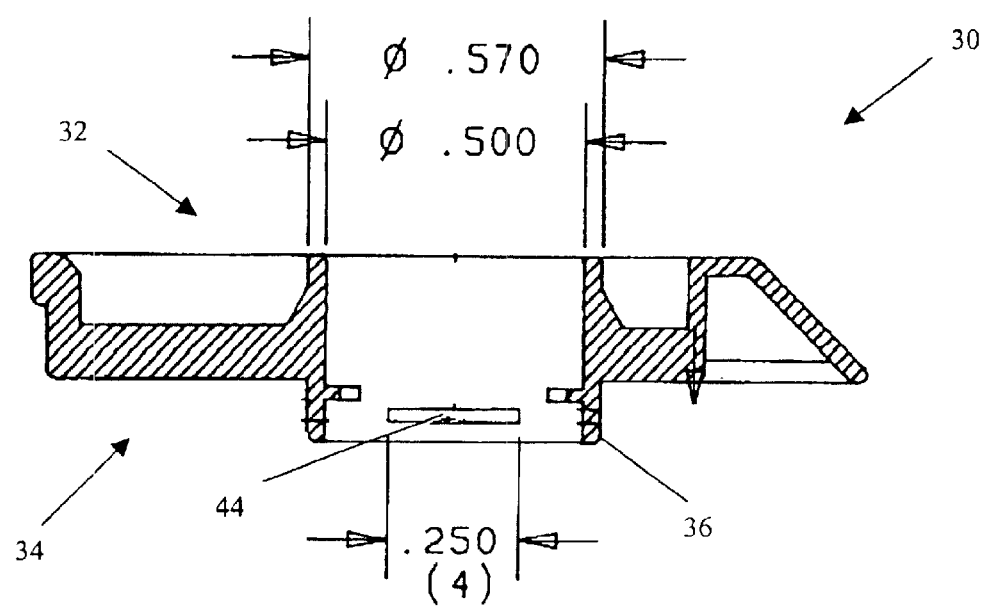
FIG. 4 is a side view of the tissue cassette of FIG. 3A along lines A—A.

As shown in FIG. 1, the sample port 26 can be attached to a removable tissue cassette 30 of the present invention. The tissue cassette 30, illustrated in greater detail in FIGS. 3A—3C, includes a cylindrical port 36 which extends from a top surface 32 through a bottom surface 34 of the cassette 30. The cylindrical port 36 creates a flow-through pathway for the cells and reagents to be delivered. The cylindrical port 36 attaches to the sample port 26 from the top surface 32 of the cassette 30 to thereby allow fluid communication between the reagent flow pathway 18 and the tissue cassette 30. Within the cylindrical port 36 are thin shelves 44 for anchoring the wax plug that will ultimately be formed in the cassette 30 (inside the cylindrical port 36 near the bottom surface 34), though it is understood that other structures such as mesh, protrusions, ridges, grooves, or surface roughness can also be included within the cylindrical port 36 for increased wax adherence. The tissue cassette 30 is designed to provide sufficient structural rigidity to eliminate the need for wax to fill the entire cassette 30, thereby conserving paraffin. It is understood that tissue cassette 30 should be constructed from a material which is resistant to degradation from alcohol, xylene or acids. Exemplary materials for forming the tissue cassette 30 include polypropylene, polypropylene with talc, and nylon. In one embodiment, the tissue cassette 30 has a length in the range of about 40–50 mm and a width in the range of about 20–30 mm. The overall depth of the cassette 30, including the port 36, is in the range of about 5–15 mm. As shown in FIG. 4, the cylindrical port 36 of the cassette 30 is approximately 0.5 inches in diameter as measured from the bottom surface 32. These dimensions allow the cylindrical port to fit into a standard embedding mold, and allow the cassette to be positioned in the holder of a standard microtome for sectioning.

Referring again to FIG. 1, the cylindrical port 36 extending out of the bottom surface 34 of the tissue cassette 30 is removably connected to a flat, ring-shaped, gasket 42. The gasket 42 can be approximately 1/16 inch in thickness, and it approximately matches the diameter (0.5 inches) and thickness of the wall of the cylindrical port 36 of the tissue cassette 30. The gasket 42 can be composed of a pliable material such as Viton™ rubber that allows the gasket 42 to form a water-tight seal with the tissue cassette 30 and resists chemical degradation upon exposure to xylene and other embedding reagents. The gasket 42 should also be sufficiently pliable to allow it to be pulled away from the hardened wax at the end of the process without deforming the hardened wax protruding from the tissue cassette.

The gasket 42 is removably connected to a filter 40 that is larger in diameter than the inner diameter of the gasket 42. The filter 40 has a pore size in the range of about 6–12 microns in diameter to allow sub-cellular debris to flow through to the filter 40 while trapping small-sized individual cells. The size of the pores of the filter can be adapted to different types of samples. For example, a sample known to contain large numbers of red blood cells and clusters of cells could be processed with a filter with 12 micron pore size to allow the individual red blood cells to pass through the filter while trapping the tissue fragments. The filter 40 can comprise a polycarbonate filter (such as, e.g., isopore™ made by Millipore corporation, Billerica, Mass.) which are smooth and prevent the cells and the wax from sticking to the filters as they are pulled away. In addition, the gasket 42, tissue cassette 30 and filter 40 can be lightly bonded together so that these three components can be quickly loaded onto the apparatus 10.

In one embodiment, the overall thickness of the tissue cassette 30 with the attached gasket 42 is in the range of approximately 5–20 mm, and preferably about 10 mm. This low-profile configuration positions the filter 40 at a location where the lowest surface of a standard tissue mold would be located if the tissue cassette 40 and gasket 42 were placed within a standard tissue mold. This tissue cassette 30 and filter 40 configuration allows the deposited cells to be automatically positioned at approximately the plane at which the microtome blade will cut the cell block, without a need for a tissue mold, since the cells are embedded within the wax block closest to the plane facing the microtome cutting blade and farthest away from the attachment site to the microtome. Since the gasket 42 and tissue cassette 30 can be produced with accurate dimensions, it is possible to have a microtome pre-set to begin sectioning at exactly the plane where cells are located. This feature of the present invention decreases the time and effort of histologists during the microtome sectioning.

As shown in FIG. 1, the filter 40 rests on a filter support 60. In one embodiment, an upper surface of the filter support 60 facing the filter 40 can be porous in its central portion so that fluids can flow through the filter 40 and filter support 60. The filter support 60 can include a non-porous flat ring surrounding the central porous portion. The filter 40 can be placed over the filter support 60 to completely cover the porous portion of the filter support 60 and extend somewhat over the non-porous part of the filter support 60. The gasket 42 can be seated on top of the outer edge of the filter 40 over the non-porous ring of the filter support 60. With this configuration, a water-tight seal can be formed between the cylindrical port 36 of the tissue cassette 30 and the filter support 60, with the filter 40 itself sandwiched therebetween. In one aspect of the embodiment (not shown), the filter support 60 can have a cylindrical extension to extend over the gasket 42 and bottom end of the cylindrical port 36 of the tissue cassette 30. With this configuration, a correct seating of the tissue cassette 30 with respect to the filter support 60, gasket 42, and filter 40 can be assured.

In another aspect, the filter support 60 can include integrated heating and cooling elements. The filter support 60 can also be configured such that heat can be conducted towards or away from the support 60 efficiently, in order to maintain the paraffin in a melted state and to speed up the paraffin hardening process. For instance, a heater associated with the filter support 60 can be used to increase the heat surrounding the support 60 during the embedding process, and decrease the heat to the support 60 when the embedding is complete and the wax is hardening. Other potential heating and cooling alternatives include maintaining the entire apparatus 10 in a heated box, or shining infrared light onto the filter 40.

The filter support 60 is removably connected to a waste container 50 for capturing the waste fluid during the embedding process, which includes fluid media containing the cell sample, and the excess embedding reagents. The different effluents can be separated from each other by mechanically moving different waste containers 50 from under the filter support 60. Alternatively, the waste container 50 can comprise a plurality of independent receptacles, each with its own solenoid clamp. Such a configuration allows the flow of a particular effluent to be selectively diverted into its respective receptacle by means of the solenoid clamps. It is contemplated that such a procedure for separating the embedding reagents in the effluent would facilitate recycling of the embedding reagents. The apparatus also decreases disposal costs since less reagents (e.g., approximately 5 ml per cell block) are used compared to other currently available methods of cell block production.

The process of making a cell block can be usefully performed manually with this invention, with many of the advantages detailed above, including: more rapid processing speed due to the increased efficiency of extraction in a flow-through system, decreased use of embedding reagents, lower risk of mislabeling, elimination of cross-contamination, elimination of the tissue mold step, and standardization of embedding or cell preservation conditions. Because the cell block embedding apparatus 10 of the present invention utilizes a flow-through design rather than simply immersing the cell fragments within embedding solutions, the efficiency of the extractions is dramatically increased, resulting in decreased use of reagents, and extremely rapid processing. In samples prepared using the apparatus of the present invention, no more than 5 ml each of alcohol, xylene and wax was needed for each cell block produced. The embedding process, when done manually, can be performed in about 10 minutes. For a manual process, the cell sample and embedding reagents could be directly delivered by pipetting to the tissue cassette 30 or to the sample port 26 under the visual supervision. It is important to load only enough cells so that the embedding reagents can flow through the cells on the filter 40. This can be done manually by adding the cells dropwise while monitoring how fast the meniscus or fluid level of fluid decreases upon application of a set negative pressure on the waste side of the filter 40. During operation of the apparatus, when the rate of meniscus, or fluid level, descent first perceptibly decreases, there is a sufficiently thick layer of cells for at least twenty 5 micron tissue sections. It has been observed that the rate of fluid level drop is faster at each of the extraction steps, presumably because the cells are made progressively more porous as water and fats are removed. It is essential to prevent the meniscus of fluid from ever passing into the filter 40 during manual performance of the embedding steps; the cells are distorted if this happens.

The apparatus 10 of the present invention can be configured for automation as well. Several strategies can be utilized to automate part or all of the cell block production with this invention. For example, it is envisioned that the flow of cell sample and reagents can be controlled with a combination of positive pressure applied upstream of the tissue cassette 30 to push the cell sample and/or embedding reagents through the filter 40, or negative pressure applied on the waste side of the tissue cassette 70 to pull the sample and/or embedding reagents through the filter. FIG. 1 illustrates an automated cell block embedding apparatus 10 in which negative pressure is applied to the waste container 50 by way of a negative pressure tube 70 that can be connected to a vacuum source. The negative pressure acts to draw the cells from the cell sample 14 through the inflow tube 20 and onto the filter 40. The negative pressure also draws the reagents through the filter 40 and over the cells to form the wax cell block. As shown, a pressure gauge 72 can be included with the outflow tube for measuring the negative pressure of the system during operation of the apparatus 10. The entire system, from the cell sample container 12 and embedding reagent reservoirs 82, 92 and 102, to the waste receptacle 50 can be made water-tight. In such a water-tight system, the application of a negative pressure at the end of the waste receptacle 70 allows solenoid tube clamps 86, 96 and 106 to control whether a cell sample 14 is delivered, or whether embedding reagents 82, 92 and 102 are delivered to the sample port 26 and thereafter to the filter 40.

In a method of operating the cell block embedding apparatus 10, a sample of cell fragments in an aqueous solution is drawn from a container 12 through the filter 40 by applying a vacuum, or negative, pressure from the waste container 50 to the inflow tube 20 until the filter pores become nearly obstructed by cell fragments. Alcohol is then pulled through the filter 40, followed by xylene and melted paraffin. After the paraffin cools, the filter 40 is peeled away from the embedded cells. The gasket 42 between the filter 40 and the tissue cassette 30 is pulled away from the tissue cassette 30 when the wax hardens, leaving a ring of wax about 1 mm in thickness protruding from the tissue cassette 30. The tissue cassette 30 is designed to accommodate the filter 40 such that the deposited cells are collected at or very near the plane at which the microtome blade will cut the cell block for sectioning. The disposable sample port 26 eliminates the risk of cross-contamination between cell blocks since the components that contact the cell sample are disposable.

Figure 2:
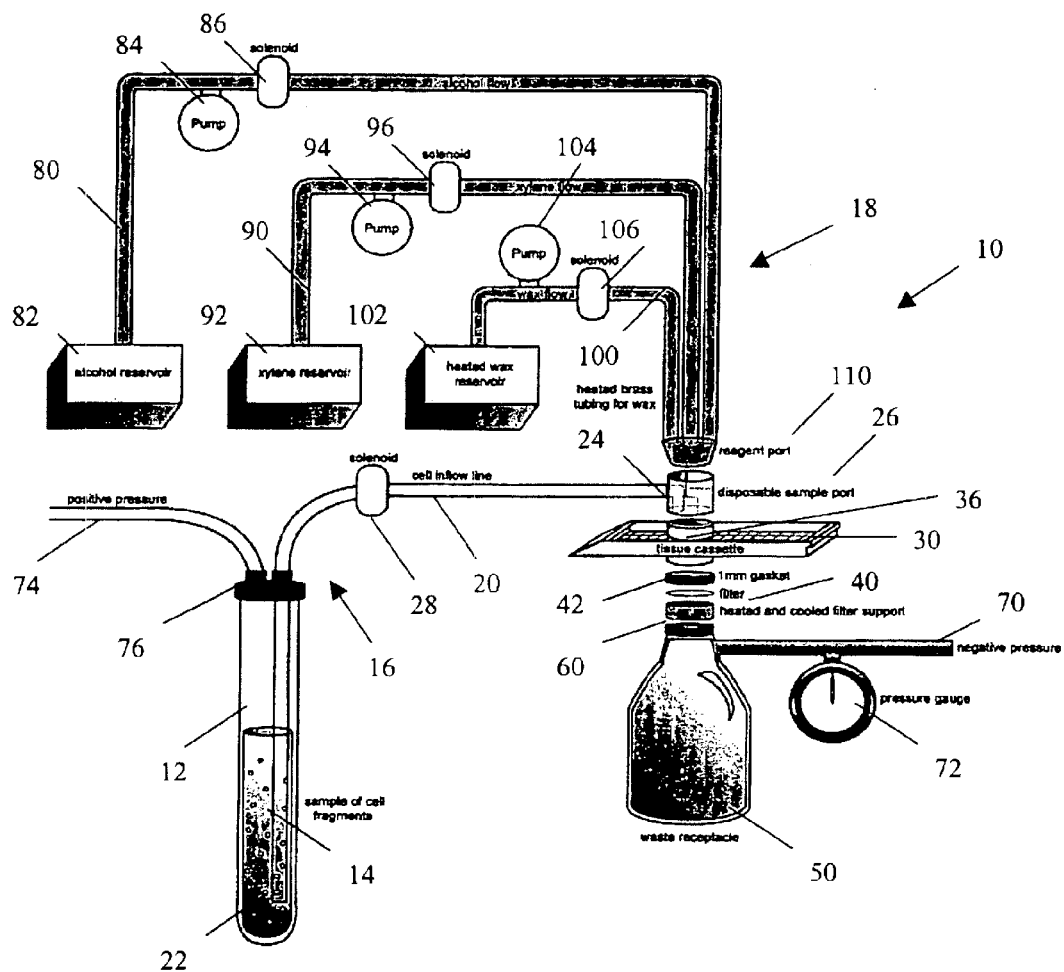
FIG. 2 is a detailed view of another embodiment of a cell block embedding apparatus of the present invention.

FIG. 2 illustrates the automated cell block embedding apparatus 10 of FIG. 1 with an additional positive pressure applied. In this embodiment, a positive pressure tube 74 can be attached to the container 12 having an airtight lid 76, as shown. The positive pressure tube 74 can be connected to a positive pressure source for delivering pressure to the container 12, which will then facilitate the movement of cells from the cell suspension in the container 12 through inflow tube 20 and thence through the sample port 24 and cassette 30 to the filter 40. A combination of positive pressure and negative pressures can be used to deliver cell sample and embedding reagents to the filter 40. As shown, the inflow tube 20 include a solenoid tube clamp 28 for ensuring an air-tight pathway. The solenoid 28 serves to keep fluids from running into the sample in a positive pressure system, or from having negative pressure pull sample instead of embedding reagents in a negative pressure system.

To automate the system, the inflow of sample and embedding reagents to the cylindrical port 36 needs to match the outflow into the waste receptacle 50 such that the meniscus of the liquids passing through the cylindrical port 36 are not pulled into the filter 40, and reagents cannot be allowed to overflow the tissue cassette 30. In a suitably water-tight system, it may be sufficient to sequentially apply positive pressure to the cell sample container 12 and embedding reagent pumps 84, 104, and 104 to force the cell sample and embedding reagents sequentially through the cylindrical port 36 and thereafter through the filter 40 to effect a useful embedding process.

Alternatively, the amount of cell sample 14 and embedding reagents delivered to the cell flow-through pathway 36 can be electronically monitored by a variety of techniques and flow rates of sample and embedding reagents can then be appropriately modulated. The meniscus or fluid level can be monitored by existing technologies, or the technologies can be specifically adapted to this particular invention For example, one mechanism to monitor the meniscus level is to reflect light at an angle to the meniscus from a laser or light emitting diode. Light sensors can monitor the line of reflectance that change as the meniscus drops. The sensors can be positioned above the tissue cassette, for example, adjacent to the sample port 26, or the sensors can be integrated into the sample port 26.

Another mechanism to monitor the fluid level is to use a disposable, immersible fiber optic cable, such as provided by ALA Scientific Instruments Inc., Westbury, N.Y. as part of their "level-lock" system. In this system, light leaks out of the cable when it is in contact with a liquid, and the drop in light intensity is proportional to the degree of immersion. A disposable fiber-optic cable could be incorporated into the cell flow pathway 16 of the tissue cassette 30 or into the sample port 24.

Yet another mechanism to monitor the fluid level would be to use capacitance-type fluid level monitors that detect fluids (including non-conducting liquids) because of their different dielectric constant compared to air. An electrical source and sensor could be positioned just above the gasket 42.

Still yet another mechanism to monitor the fluid level would be to position a beam of light horizontally through the lower part of the cell flow pathway immediately above the gasket 42 in a translucent tissue cassette 30. A light sensor placed on the opposite side of the cell flow pathway could detect a change in intensity as the meniscus passed through the light beam.

And yet another mechanism to monitor flow rates would be to weigh the effluent that passes through the filter. Delivery of the sample and embedding reagents could be coupled to the weight of the effluent such that the amount of sample or embedding reagents within the cell flow pathway of the tissue cassette is maintained between two levels.

Automated loading of the appropriate amount of cell sample 14 on the filter 40 could be achieved by a variety of mechanisms. In a suitable water-tight configuration with solenoid tube clamps 86, 96, 106 closed, application of a modest negative pressure at the waste end of the invention could deliver the cell sample 14 to the filter 40. A pressure gauge 72 could trigger the release of the negative pressure when negative pressure is built up to a certain point indicative of the blockage of some of the pores of the filter 40. This mechanism would be similar to those described in U.S. Pat. Nos. 6,225,125 and 6,010,909.

Alternatively, application to the cell sample container 12 of a short pulse of positive pressure, as shown in FIG. 2 could force an aliquot of sample into the cylindrical port 36 of the tissue cassette 30. The amount of cells delivered could then be estimated by the rate of flow through the filter 40. To facilitate this process in which only small aliquots of cell sample is delivered to the filter 40, it would be feasible to pump in a larger volume of alcohol or saline with each small aliquot of cell sample delivered. The switching from alcohol to xylene to wax can be set for a certain volume of reagents to be pumped. In studies using the apparatus 10 of the present invention, we repeatedly have determined that 5 ml of each of these reagents is sufficient for proper embedding. It could also be feasible to monitor the effluent for changes in refractive index that would indicate that extractions have gone to completion. That is, refractometers can be positioned downstream of the cell sample in the waste container 50 and the difference in the refractive index between water, alcohol, and xylene could be used to determine whether all of the reagent (e.g., water, alcohol, xylene, etc.) has been removed.

It is understood that, while three different reagent delivery tubes are shown and described, the reagent flow pathway 18 can comprise any number and combination of reagent delivery tubes. For example, it may be advantageous to include a saline reservoir with a flow line to the reagent port 110 to wash away proteins from cell samples 14 contained in a physiologic saline solution. It may also be useful to include an acid reservoir and flow line to the reagent port 110 be able to effect a decalcification of a sample. Excellent quality pre-staining using the present apparatus can also be achieved with the present invention. For example, the reservoirs could include hematoxylin, eosin and distilled water to allow a pre-staining of the cell sample, thereby saving time due to eliminating the need for staining an eventual paraffin section. Eosin is also convenient to include during the alcohol extractions because the eosin makes the cell sample apparent to the histologist who cuts the paraffin section, allowing the histologist to gauge the quality and quantity of the cells in sections as they are being cut with a microtome.

By placing the filter at the plane of the tissue section, the process of manual embedding is eliminated, and the time required for a technician to find the plane of the cells in the embedded block is reduced. Since no other supporting matrix material is used, the cell fragments are not "diluted" with matrix, and each tissue section can therefore show a higher concentration of cells. Nevertheless, in some situations it may be desirable to place the final embedded cell sample into a tissue mold for re-melting and re-hardening (step 11 of the generic cell-block procedure described in the background). This could be done in an automated fashion. The function of the remelting and re-hardening step would be to allow a thin layer of wax to cover the bottom of the cells to facilitate the "facing in" step of microtome sectioning, which increases the number of useable sections that can be cut from a cell block.

It is understood that the apparatus is configured such that the components are easily removable from one another. This is desirable so that a technician can quickly and easily replace used or worn components in an efficient manner. Further, the sample port 26, cell inflow tube 20 and its removable outlet end 24, and the cell sample container 12 of the present invention are all disposable. This allows a one-time use of each of these components for processing one single sample, thereby preventing contamination while processing subsequent cell samples.

While the cell block embedding apparatus 10 and method of using the apparatus are described herein as a flow-through system, it is contemplated that the invention could still offer advantages over existing technology even if the cell flow pathway 16 did not pass through the tissue cassette 30. For instance, it is envisioned that the cells could still be efficiently and quickly embedded in a temporary chamber overlying the filter 40. Afterwards, the temporary chamber could be subsequently remelted in a standard tissue mold, and this remelting could be automated.

It is further contemplated that a bar-code reader (not shown) could be included with the invention to match the label of the cell sample with a label on the tissue cassette, and thereby eliminate mislabeling.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A flow-through cell block embedding apparatus, comprising:
   a sample port;
   a cell flow pathway defined by an inflow tube that is adapted to be coupled to the sample port, wherein the inflow tube is effective to deliver cell fragments from a cell sample to the sample port;
   a tissue cassette in fluid communication with the sample port, the tissue cssette including a removeable and replacable filter such that upon the application of pressure, the cell fragments are drawn from the cell sample through the inflow tube to the sample port and deposited onto the filter;
   a reagent port in fluid communication with the sample port; and
   a plurality of reagent delivery tubes adapted to be coupled in fluid communication to the reagent port, wherein the plurality of reagent tubes are effective to deliver a plurality of reagents to the reagent port such that upon the application of pressure, the reagents are drawn through the reagent delivery tubes to the reagent port to the deposited cell fragments on the filter.

2. The apparatus of claim 1, wherein the tissue cassette is in fluid communication with the sample port and the reagent port such that the cell fragments are automatically deposited near the plane to be sectioned by a microtome.

3. The apparatus of claim 1, wherein the pressure applied to the reagent flow pathway is a negative pressure.

4. The apparatus of claim 1, wherein the pressure applied to the reagent flow pathway is a positive pressure.

5. The apparatus of claim 1, wherein the pressure applied to the cell flow pathway is a negative pressure.

6. The apparatus of claim 1, wherein the pressure applied to the cell flow pathway is a positive pressure.

7. The apparatus of claim 1, wherein the reagent flow pathway includes a reagent delivery tube for delivering a reagent selected from the group consisting of alcohol, xylene, hot paraffin, distilled water, saline, acid, hematoxylin, eosin, and immunohistochemistry reagents.

8. The apparatus of claim 7, wherein the reagent flow pathway includes a heated reagent delivery tube for delivering hot paraffin to the sample port.

9. The apparatus of claim 1, wherein each reagent delivery tube further includes a pump for regulating the flow of reagent through the tube.

10. The apparatus of claim 1, wherein each reagent delivery tube further includes a solenoid tube clamp for forming an airtight pathway.

11. The apparatus of claim 1, wherein the filter comprises polycarbonate.

12. The apparatus of claim 1, wherein the tissue cassette further includes a cylindrical port extending through the cassette configured for attachment to the filter.

13. The apparatus of claim 12, wherein the cylindrical port is configured for attachment to the sample port.

14. The apparatus of claim 1, further including a waste container for collecting at least one of the plurality of reagents.

15. The apparatus of claim 14, wherein the waste container includes a port for connecting to a pressure source.

16. The apparatus of claim 15, wherein the port further includes a pressure gauge.

17. The apparatus of claim 1, wherein the sample port is disposable.

18. The apparatus of claim 1, wherein the apparatus is fully automated.

* * * * *